United States Patent
Le et al.

(10) Patent No.: US 11,737,477 B2
(45) Date of Patent: Aug. 29, 2023

(54) METHODS OF BINDING TEXTURED SUBSTRATES USING MYCELIUM-PRODUCING FUNGI AND FOOD PRODUCTS FORMED THEREFROM

(71) Applicant: TERRAMINO INC., Berkeley, CA (US)

(72) Inventors: Kimberlie Le, Berkeley, CA (US); Joshua Nixon, Berkeley, CA (US); Marisa Yang, Berkeley, CA (US); John Frelka, Berkeley, CA (US)

(73) Assignee: TERRAMINO INC., Berkeley, CA (US)

( * ) Notice: Subject to any disclaimer, the term of this patent is extended or adjusted under 35 U.S.C. 154(b) by 160 days.

(21) Appl. No.: 16/991,488

(22) Filed: Aug. 12, 2020

(65) Prior Publication Data

US 2021/0045410 A1 Feb. 18, 2021

Related U.S. Application Data

(60) Provisional application No. 62/885,392, filed on Aug. 12, 2019.

(51) Int. Cl.
*A23L 3/00* (2006.01)
*A23J 3/22* (2006.01)
(Continued)

(52) U.S. Cl.
CPC .............. *A23J 3/227* (2013.01); *A23L 3/00* (2013.01); *A23L 5/42* (2016.08); *A23L 31/00* (2016.08); *C12N 1/14* (2013.01); *A23V 2002/00* (2013.01)

(58) Field of Classification Search
CPC .. A23J 3/227; A23L 5/42; A23L 31/00; A23L 3/00; C12N 1/14; A23V 2002/00
(Continued)

(56) References Cited

U.S. PATENT DOCUMENTS 4,265,915 A 5/1981 MacLennan et al.
4,466,988 A 8/1984 Towersey et al.
(Continued)

FOREIGN PATENT DOCUMENTS

CN 106290533 A 1/2017
EP 2835058 A1 * 2/2015 ................ A23J 1/04
(Continued)

OTHER PUBLICATIONS

Han, "How to Make Tempeh", Published on Jun. 8, 2019. Retrived on Sep. 24, 2020 on <URL: https://www.thekitchn.com/how-to-make-tempeh-cooking-lessons-from-the-kitchn-202369> Whole document, images of the final tempeh product.

*Primary Examiner* — Hamid R Badr
(74) *Attorney, Agent, or Firm* — Holzer Patel Drennan

(57) ABSTRACT

Described herein are various embodiments of methods for binding together textured substrates using mycelium-producing fungi. The method can generally include providing a textured substrate, such as a textured protein substrate, that may or may not be subjected to various pre-processing steps used to help promote mycelium growth inside, outside or inside and outside of the textured substrate, inoculating the textured substrate with mycelium-producing fungi, and growing mycelium inside, outside, or inside and outside of the textured substrate to bind the textured substrate. The bound textured substrate can be used as a high protein food, such as meat substitutes, meat analogues, or seafood analogues. In some embodiments, the mycelium-producing fungi is used to bind together multiple textured substrates to form larger composite food products.

17 Claims, 6 Drawing Sheets

(51) Int. Cl.
  *C12N 1/14*   (2006.01)
  *A23L 5/42*   (2016.01)
  *A23L 31/00*  (2016.01)
(58) Field of Classification Search
  USPC .......................................................... 426/7
  See application file for complete search history.

(56) References Cited

U.S. PATENT DOCUMENTS

| | | |
|---|---|---|
| 7,045,160 B1 | 5/2006 | De et al. |
| 8,672,245 B2 | 3/2014 | Finnigan et al. |
| 10,172,381 B2 | 1/2019 | Vrljic et al. |
| 2003/0157219 A1 | 8/2003 | Bijl et al. |
| 2018/0014567 A1 | 1/2018 | Finnigan et al. |
| 2019/0037895 A1 | 2/2019 | Shiraishi |
| 2019/0059431 A1 | 2/2019 | Kozubal et al. |

FOREIGN PATENT DOCUMENTS

| | | | | |
|---|---|---|---|---|
| EP | 2835058 A1 | 2/2015 | | |
| JP | H1075739 A | 3/1998 | | |
| JP | 2020014427 A | 1/2020 | | |
| WO | 2000065029 A1 | 11/2000 | | |
| WO | 2013087558 A1 | 6/2013 | | |
| WO | WO-2013087558 A1 * | 6/2013 | ................ | A23J 3/18 |
| WO | 201802587 | 1/2018 | | |
| WO | 2020154634 A1 | 7/2020 | | |

\* cited by examiner

METHODS OF BINDING TEXTURED SUBSTRATES USING MYCELIUM-PRODUCING FUNGI AND FOOD PRODUCTS FORMED THEREFROM

CROSS-REFERENCE TO RELATED APPLICATIONS

The present application claims priority under 35 U.S.C. § 119(e) to U.S. Provisional Patent Application No. 62/864,946, filed Aug. 12, 2019, the entirety of which is hereby incorporated by reference.

TECHNICAL FIELD

The present application relates to methods of binding textured substrates, such as textured protein substrates, using fungal mycelium growth. The bound textured substrates formed by the methods described herein can be used as a high protein food, such as meat substitutes, meat analogues, or seafood analogues.

BACKGROUND

In the formation of meat and seafood alternatives, gums and/or gelling agents are often used to hold together the base component (e.g., protein component) of the food product. For example, some meat alternatives use potato and egg white protein as a gelling agent, while other meat alternatives use starches or gums as binding agents. Less protein-rich foods often use sugars as binding agents.

However, use of gums and/or gelling proteins in meat and seafood alternatives can present several disadvantages. For example, the use of gums and/or gelling proteins results in a food product including more ingredients, which can raise issues with consumers looking for limited-ingredient and/or minimally processed foods. The use of these additional ingredients can also complicate the manufacturing process, which thereby increases the cost of production. Additionally, gums and/or gelling agents provide minimally effective binding of base components. Furthermore, the gums and/or gelling agents generally don't add to the overall protein content of the food product, but will instead add less desirable carbohydrates.

Accordingly, a need exists for improved binding components and improved methods of manufacturing food products using the improved binding components.

SUMMARY

Described herein are various embodiments of methods for binding together textured substrates using mycelium-producing fungi. The method can generally include providing a textured substrate, such as a textured protein substrate, that may or may not be subjected to various pre-processing steps used to help promote mycelium growth inside, outside or inside and outside of the textured substrate, inoculating the textured substrate with mycelium-producing fungi, and growing mycelium inside, outside, or inside and outside of the textured substrate to bind the textured substrate. The bound textured substrate can be used as a high protein food, such as meat substitutes, meat analogues, or seafood analogues. In some embodiments, the mycelium-producing fungi is used to bind together multiple textured substrates to form larger composite food products.

DETAILED DESCRIPTION

Figure 1A:
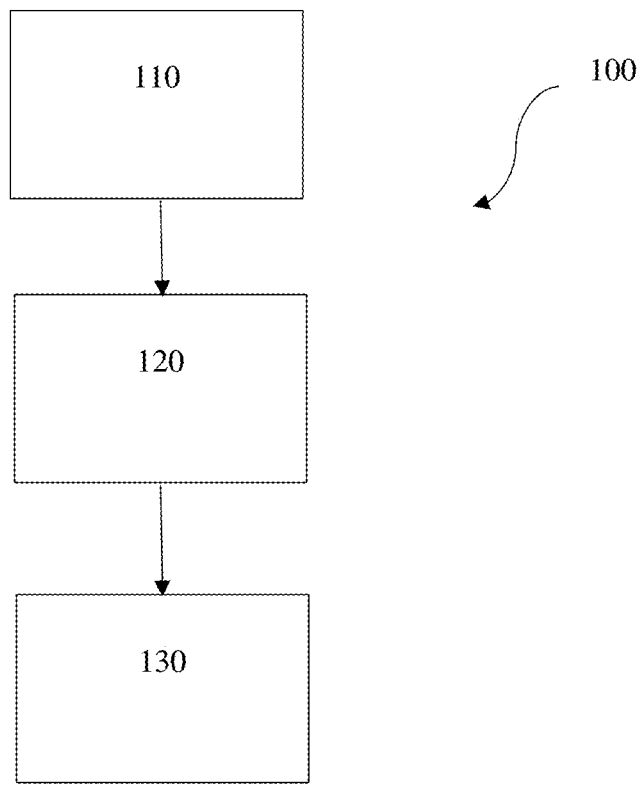
FIG. 1A is a flow diagram illustrating a method for forming a bound textured substrate according to various embodiments described herein.
Figure 1B:
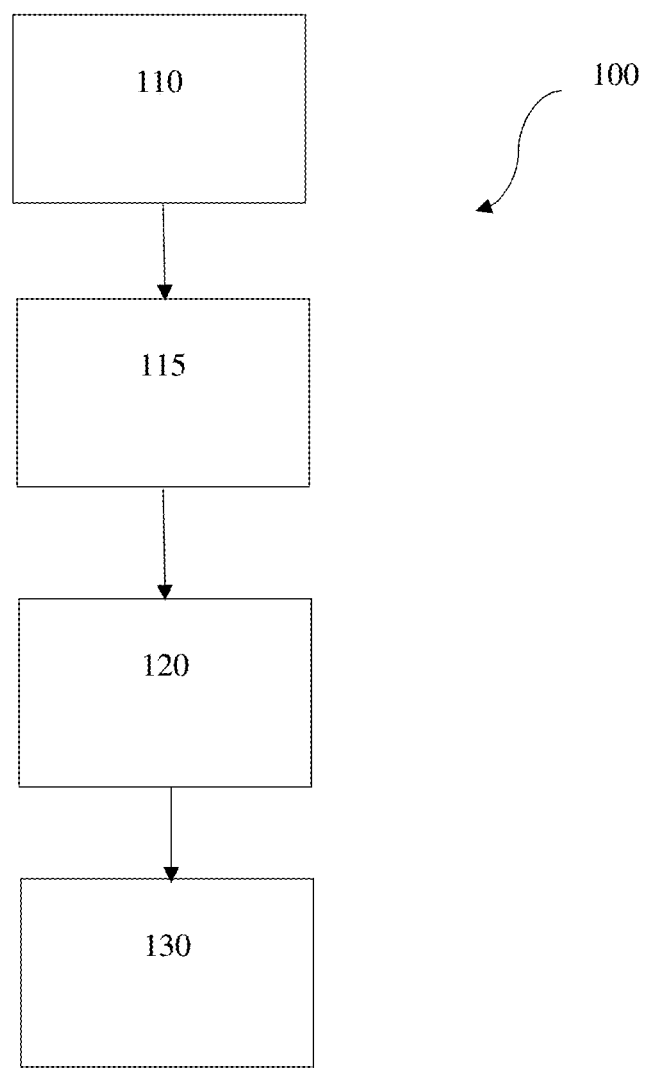
FIG. 1B is a flow diagram illustrating a method for forming a bound textured substrate according to various embodiments described herein.

With reference to FIG. 1, a method 100 for forming a bound textured substrate generally comprises a step 110 of providing a textured substrate, a step 120 of inoculating the textured substrate with mycelium-producing fungi, and a step 130 of growing mycelium within and/or around the textured substrate to bind the substrate. Generally speaking, the method 100 provides a means for taking a substrate, such as a protein substrate, that is textured at a local level, and binding the substrate through the growth of mycelium in and/or around the substrate to thereby create a matrix within and/or around the substrate. The matrix created in and/or around the substrate binds the substrate and creates texturization at a macro level. The manner in which the mycelium is grown in and/or around the substrate may be controlled to achieve desired end results with respect to, for example, texturization, stability, and dimensionality. The method 100 generally allows for the creation of food products that are high in protein and can serve as, for example, meat substitutes, while also providing a food product having improved binding, stability, texture, and a wider range of sizes and shapes.

In step 110, a textured substrate is provided. Any textured substrate suitable for use in food products and which has a structure suitable for receiving mycelium growth can be used. In some embodiments, the textured substrate is a textured protein substrate. One non-limiting example of a suitable textured protein substrate is textured vegetable protein (TVP), while other non-limiting examples include plant-based textured substrates. TVP is formed using an extrusion process by which a pressurized molten protein mixture is extruded to cause rapid expansion into a fibrous, spongy matrix. As such, the TVP has a generally porous network into which mycelium can grow to form a matrix in and around the TVP to improve the overall binding of the TVP substrate. The extrusion process used to form the fibrous spongy matrix, TVP provides the texturing to the TVP substrate, and similar or other processing methods can be used to provide texture to other types of substrates. Generally speaking, the term textured as used herein when describing substrates generally means having a texture similar to the texture of TVP wherein texturing is obtained via processing, or similar texturing to TVP that may occur naturally in the substrate (such as in naturally fibrous material), or to texturing similar to TVP provided by the mycelium growth itself.

In some embodiments, the textured substrate is fungi-based. For example, the textured substrate can be a fungal biomass. The textured substrate may also be a processed fungal fermented composition. As used herein, the term "fungal-fermented composition" generally includes any food or beverage composition that uses fungus to ferment one or more ingredients of the food or beverage composition during the process of making the food or beverage composition. Reference to "fungal-fermented composition" includes both alcoholic and non-alcoholic compositions. Non-limiting examples of fungal-fermented beverages include, but are not limited to: Sake, Mirin, Sochu, Soju, Dansul, Jiuniang, Cheongju, Amazake, Awamori, Doburoku, Shaosing-chu, Takju, Yakju, Makgeolli, Samsu, Tapai, Tapuy, Thai rice wine, Ruhi, Pachwai, and Brem Bali. More generally, the fungal fermented beverage can be any alcoholic beverage produced by saccharifying a plant material with a filamentous fungus in which a byproduct containing said filamentous fungus is produced. Non-limiting examples of fungal-fermented foods include, but are not limited to, soy sauce, tempeh and miso. The fungal-fermented composition serving as the textured substrate may be in a finished product state (i.e., suitable for sale, distribution, human consumption, etc.), a pre-finished product state (i.e., where further processing steps are to be carried out prior to the composition being sold, distributed, consumed, etc.), or may be a byproduct formed during the production of another composition. For example, the fungal fermented composition can be obtained from sake kasu, either as whole sake kasu, sake kasu subjected to processing aimed at increasing the concentration of fungal material, or a fungal biomass separated from sake kasu. Processed or grown fungal protein biomass in the form of a substrate can also be used. Crushed or ground fungal material, such as crushed or ground mushrooms, can also be used as the substrate material.

The size and shape of the substrate provided in step 110 is generally not limited. In some embodiments, the substrate is in the form of blocks, flakes, chunks, nuggets, strips or the like. The size of the substrate provided in step 110 is generally increased via the mycelium growth step 130 discussed in greater detail below, either by forming a matrix within and/or around the base substrate, or by binding together two or more substrates into a composite material.

In step 120, the textured substrate provided in step 110 is inoculated with a mycelium-producing fungi. The inoculation step 120 generally includes any manner of adding the mycelium-producing fungi to the textured substrate so that subsequent steps can be carried out to grow the mycelium and form a matrix within and/or around the substrate. Generally speaking, mycelium-producing fungi is added to the substrate through the addition of spores into and/or on the substrate, though mycelium can also be added directly into the substrate. In some embodiments, inoculation is carried out so that the mycelium-forming fungi is located throughout the substrate, both within the substrate (i.e., within pores and void spaces in the substrate) and on the surfaces of the substrate. Alternatively, selective inoculation can also be used such that spores are introduced only to specific areas or regions of the substrate.

Any manner of inoculating the substrate with spores of the mycelium-producing fungi can be used. In some embodiments, the spores are in a suspension and the suspension is introduced into and on the substrate to deliver spores to different portions of the substrate. As discussed in greater detail below with respect to pre-processing steps that may be carried out on the substrate, spores can be introduced into the substrate via a spear used to poke holes in the substrate. In such embodiments, the spear can be coated with spores so that as the spear penetrates the substrate, spores are introduced into the interior portion of the substrate. Sprinkling dry spores into or onto the substrate can also be used.

Any fungal material can be used in step 120 provided that the fungal material is capable of growing mycelium that will serve to bind the substrate. Exemplary though non-limiting examples of fungi that can be used include those from the *Rhizopus, Aspergillus*, or *Pleurotus* genus of fungi. Specific examples of species of fungi that can be used include, but are not limited to *Rhiszopus oligosporus, Rhizopus oryzae* and *Aspergillus oryzae*. Other filamentous microorganisms and fungi may also be used. In some embodiments, the fungi selected for binding the substrate is of a strain that consumes fat during fermentation (rather than carbohydrates) such that the growth process is simplified. For example, in such embodiments, it may be unnecessary to add carbohydrates to the substrate prior to mycelium growth, which makes the growth process simpler for a low carbohydrate food product.

Where the textured substrate is fungal biomass, processed fungal protein, or some other fungi-based substrate material, the fungal spores inoculated into the substrate may be either the same fungus as the substrate or different fungi. Regardless of the substrate material, the substrate can be inoculated with one fungus or multiple types of fungi.

In step 130, mycelium is grown so as to form a matrix in and around the substrate to bind the substrate. More specifically, the mycelium grows in a network that binds to itself and the material of the substrate. Mycelium growth is generally carried out via fermentation of the fungal material inoculated into the substrate in step 120. As such, step 130 is generally carried out under conditions that promote fermentation of the fungal material, such as providing an oxygen environment and/or providing carbohydrates and/or providing fats. For example, an oxygen-enriched environment can be provided to promote mycelium growth. In some embodiments, an oxygen-enriched environment helps to produce denser fungal mycelium growth, which may create a stronger bound material that has a higher protein concentration. As discussed in greater detail below, pre-processing of the substrate can be also carried out in order to improve conditions for fermentation and/or promote fermentation.

As the mycelium grows in step 130, the size of the substrate increases via the matrix of mycelium formed in and around the substrate. Additionally, the growth of the mycelium in step 130 may generally carry forward the local texturization such that the enlarged substrate has similar texturization, but on a macro scale. As described in greater detail below, mycelium growth can also be carried out to bind together two or more substrates.

While FIG. 1A illustrate a general method 100 for binding substrates with mycelium, the method can be altered and improved via various additional processing steps carried out during the method shown in FIG. 1. For example, with respect to FIG. 1B, an additional substrate pre-processing step 115 can be carried out in order to condition the substrate in ways that may promote mycelium growth. Substrate pre-processing step 115 is generally not limited, and may include any manner of treating or otherwise conditioning the substrate to improve mycelium growth.

In some embodiments, substrate pre-processing step 115 includes compacting the substrate prior to inoculating the substrate. Any manner of compacting the substrate can be used. An aim of compacting the substrate prior to inoculation can be to densify the substrate, align fibers in the substrate, and/or shape and direct the micromorphology of growth of the fungi.

In some embodiments, the substrate is aerated in order to improve oxygen flow through the substrate, which can therefore promote improved fermentation in step 130. Any manner of aerating the substrate can be used. In some embodiments, the substrate is poked repeatedly in different locations with a spear, needle or the like. Selective poking of the substrate can channel oxygen to specific zones or areas of the substrate where increased and/or improved fermentation is desired. Modification of the substrate to create enclose oxygen (i.e., trap oxygen within voids within the substrate) can also be carried out as part of pre-processing step 115.

Additionally, and as mentioned previously, a spear, needle, or the like used to aerate the substrate can be coated with mycelium-producing fungal spores such that the pre-processing step 115 also serves as at least part of the inoculation step 120. As with selectively poking the substrate to create channels for oxygen flow to specific areas within the substrate, the use of the spear, needle or the like to inoculate the substrate can also be carried out selectively to ensure specific placement of spores within specified zones in the substrate.

In some embodiments, a fat and/or oil component is added to the substrate as part of pre-processing step 115. Any manner of adding the fat and/or oil component to the substrate can be used, such as via injection. The fat and/or oil component can be added throughout the substrate or selectively to specified zones within the substrate. When added to the substrate, the fat and/or oil component can be adsorbed into the substrate. The fat and/or oil component can be added in order to add desirable components to the resulting food product formed from the substrate.

Similar to the preceding paragraph, pre-processing step 115 may include adding carbohydrates to the substrate. Any manner of adding the carbohydrates to the substrate can be used. The carbohydrates can be added throughout the substrate or selectively to specified zones within the substrate. An aim of adding carbohydrates to the substrate can be to provide the fungi with additional energy to grow during the growth stage (in addition to carbohydrates that may be naturally occurring within the substrate). In some embodiments, the amount of carbohydrates added to the substrate is a specified amount pre-determined to be the exact amount needed for mycelium growth such that little to no carbohydrates are left in the substrate after the fungal growth step.

In some embodiments, a nitrogen source, such as protein or amino acids or an ammonia compound, for instance in the form of a protein isolate, is added to the substrate as part of pre-processing step 115. Any manner of adding the protein to the substrate can be used. The protein can be added throughout the substrate or selectively to specified zones within the substrate. The protein component can be added in order to add desirable components to the resulting food product formed from the substrate.

Flavoring and/or coloring may also be added to the substrate as part of a pre-processing step 115. Any type and combination of flavors and/or colors can be added to the substrate using any suitable methods, including injection. Flavoring and/or coloring can be added throughout the substrate, or selectively to specific zones of the substrate. Subsequently during growth, the fungi may uptake the color and/or flavor, in which case such coloring and/or flavoring becomes part of the grown mycelium.

In some embodiments, pre-processing step 115 may include sterilizing the substrate prior to inoculation and mycelium growth.

The above-described processes that may be carried out as pre-processing step 115 can be carried out individually or in any combination and in any order.

Figure 1C:
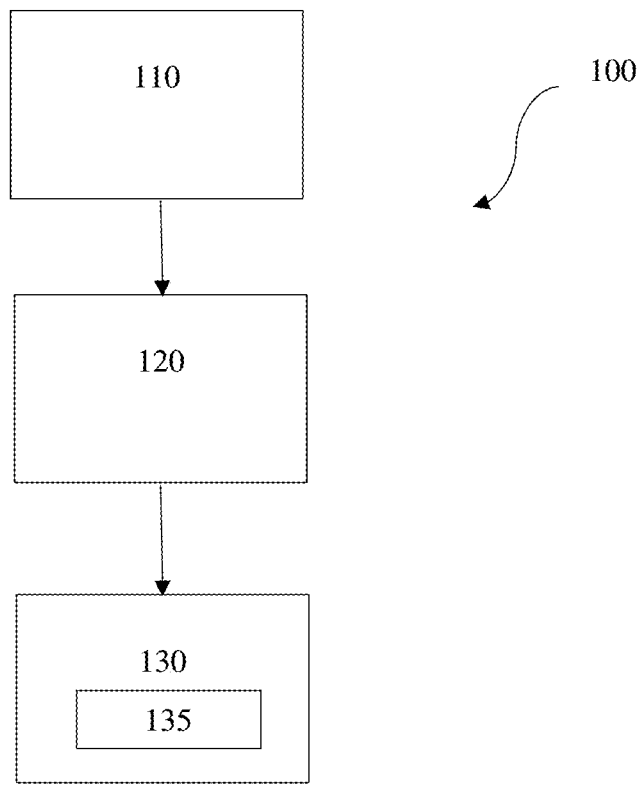
FIG. 1C is a flow diagram illustrating a method for forming a bound textured substrate according to various embodiments described herein.

With reference now to FIG. 1C, the method 100 may also be modified from the base method 100 shown in FIG. 1A by adding a processing step 135 carried out concurrently with the mycelium growth step 130. The in-growth processing step 135 can be carried out throughout the mycelium growth step 130, at a specified time during the mycelium growth step 130, or at different intervals during the mycelium growth step 130. An objective of the in-growth processing step 135 may be, e.g., to promote continued mycelium growth and/or to condition the substrate for subsequent use as a food product.

In some embodiments, in-growth processing step 135 includes compacting the substrate during mycelium growth. Because mycelium growth is occurring during compaction, compaction will serve to compact both the original substrate and any mycelium grown at the point of compaction. Any manner of compacting the substrate can be used. In some embodiments, compaction is carried out continuously throughout the mycelium growth, or at intervals during mycelium growth. An aim of compacting the substrate during mycelium growth is to densify the entire mass and to make the macrotextures more similar to meat and other food products. For example, compacting can be carried out to align the fibers in the substrate or to create distinct layering patterns.

In some embodiments, a fat and/or oil component is added to the substrate as part of in-growth processing step 135. As with step 115, any manner of adding the fat and/or oil component to the substrate during mycelium growth can be used, such as via injection. The fat and/or oil component can be added throughout the substrate or selectively to specified zones within the substrate. When added to the substrate, the fat and/or oil component can be adsorbed into the substrate. The fat and/or oil component can be added in order to add desirable components to the resulting food product formed from the substrate.

Carbohydrates may also be added during growth of mycelium as part of processing step 135. When carbohydrates are added during mycelium growth, such as via injection, the carbohydrates can be added at intervals during growth or continuously throughout the mycelium growth step.

Flavoring or coloring, or both flavoring and coloring, may also be added during the growth of mycelium as part of processing step 135. The flavoring and/or coloring can be added to the substrate, for example, via injection, with an aim of preparing the substrate being bound together by the mycelium for use as a food product. The fungi may uptake the color or flavor, in which case coloring and/or flavoring become part of the grown mycelium.

Protein may also be added during the growth of the mycelium as part of the processing step 135. The protein can be added to the substrate in any suitable manner, with an aim of adding desirable components to the substrate they may subsequently be used as a food product.

Figure 1D:
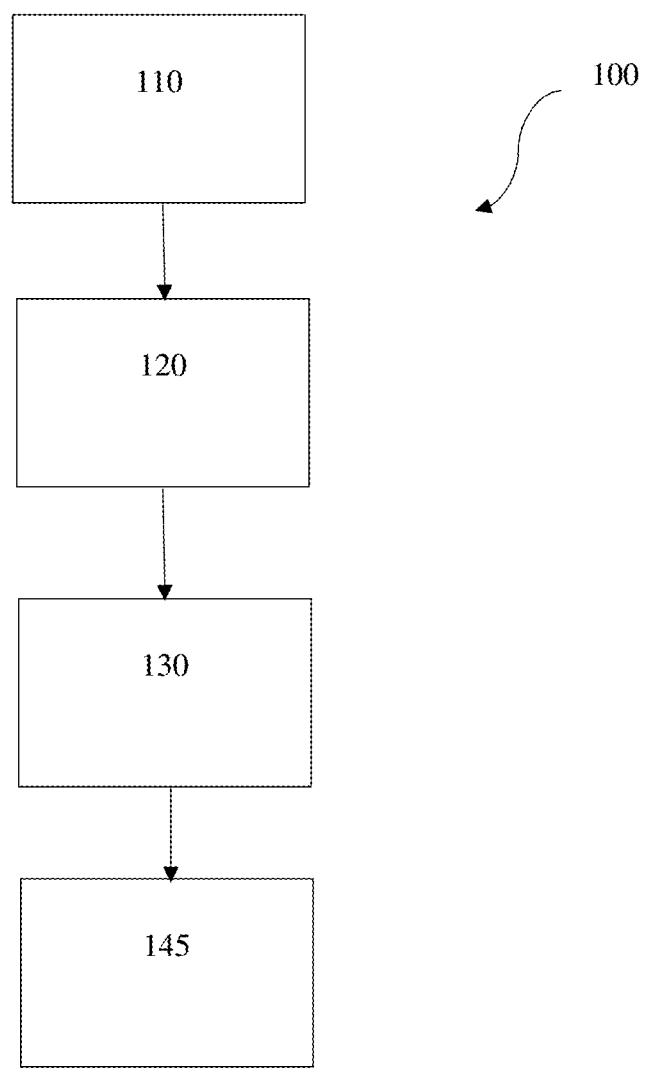
FIG. 1D is a flow diagram illustrating a method for forming a bound textured substrate according to various embodiments described herein.

With reference now to FIG. 1D, the method 100 may also be modified from the base method 100 shown in FIG. 1A by adding a post-processing step 145 carried out after the mycelium growth step 130. An objective of the post-processing step 135 may be, e.g., to condition the substrate for subsequent use as a food product.

In some embodiments, in-growth processing step 135 includes compacting the substrate after mycelium growth. Because mycelium growth has been completed, compaction will serve to compact both the original substrate and the grown mycelium that has formed a matrix within and around the substrate. Any manner of compacting the substrate can be used. An aim of compacting the substrate after mycelium growth is to create a denser material for food consumption that has more nutrients and more favorable texture and which can therefore be used as a, e.g., meat substitute.

In some embodiments, a fat and/or oil component is added to the substrate as part of post processing step 145. As with steps 115 and 135, any manner of adding the fat and/or oil component to the substrate after mycelium growth can be used, such as via injection. The fat and/or oil component can be added throughout the substrate or selectively to specified zones within the substrate. When added to the substrate, the fat and/or oil component can be adsorbed into the substrate and/or adsorbed into the now created fungal matrix. The fat and/or oil component can be added in order to add desirable components to the resulting food product formed from the substrate.

Flavoring and/or coloring may also be added after growth of mycelium as part of processing step 145. The flavoring and/or coloring can be added to the substrate, for example, via injection, with an aim of preparing the substrate bound together by the mycelium for use as a food product.

While FIGS. 1A-1D generally utilize a step 110 in which a generic textured substrate is provided, the methods show in FIG. 1A-1D can also include embodiments where the substrate provided has already been modified to accomplish some or all of the processing described in processing steps 115, 135, and 145. For example, in some embodiments, the manner in which the textured substrate is made includes the incorporation of inoculant, fat, oil, carbohydrates, protein, coloring, and/or flavoring into the material being processed into a textured substrate such that the textured substrate provided in step 110 already has incorporated therein one or more of inoculant, fat, oil carbohydrates, protein, coloring, and flavoring.

Figure 1E:
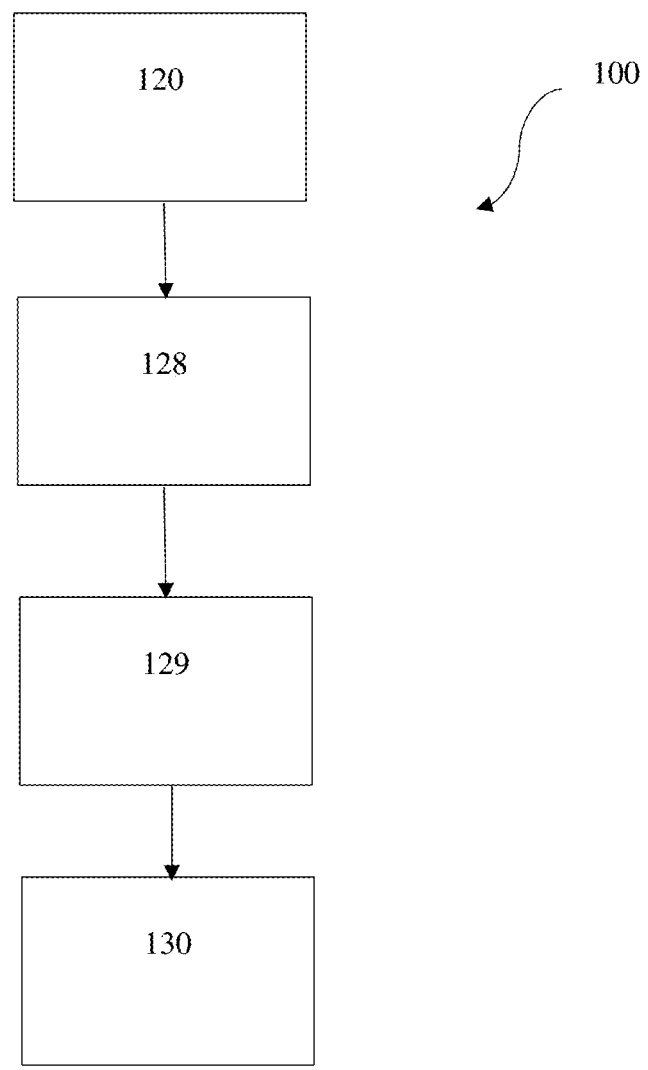
FIG. 1E is a flow diagram illustrating a method for forming a bound textured substrate according to various embodiments described herein.

As described above with respect to step 130 in FIGS. 1A-1D where mycelium growth is carried out, fermentation is used to grow fungi, and more specifically, fungal mycelium. With reference to FIG. 1E, a modification to the general method 100 of FIG. 1A is to carry out a portion of mycelium growth via liquid-state fermentation 128 (during which the substrate is grown) followed by a filtration step 129 in which the liquid is removed, and then solid-state fermentation 130 is carried out for further mycelium growth. In this embodiment, filtration is carried out to remove liquid from the substrate grown during the liquid fermentation step 128. The specific manner of filtering the liquid is not limited, provided that the fungi is not killed via the filtration process. Because the fungi remain alive after filtration step 129, additional solid-state fermentation can be carried out in step 130 to continue the growth of the mycelium. In order to further promote this solid-state fermentation step 130, the filtration may be carried out in such a way as to leave behind in the substrate the nutrients need to continue fungal growth. Additionally or in the alternative, it may also be useful to provide additional nutrients (e.g., oil, fats, carbohydrates, etc.) to continue fungal growth in solid state. In an alternative embodiment, a new species or the same species again is introduced to the substrate after the liquid state fermentation, and the inoculant is used to carry out the solid-state fermentation. A benefit of this alternative is that it is no longer necessary to take steps to ensure that the initial fungi (i.e., the fungi responsible for the liquid state fermentation) remains alive after filtration. In either embodiment, the process by which liquid state and solid-state fermentation are carried out as part of the mycelium growth can help to ensure that the fungi grow in close proximity to one another, thereby creating a substrate bound by a compact and dense mycelium network.

Figure 2:
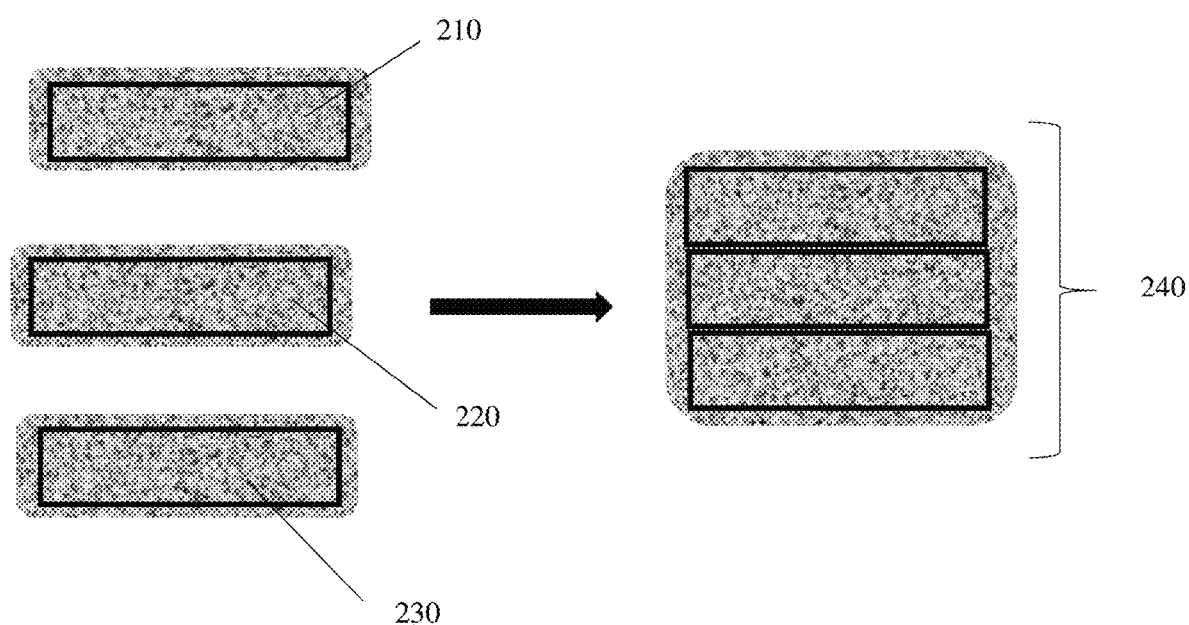
FIG. 2 is a schematic illustration of a method of binding together two or more textures substrates according to various embodiments described herein.

As discussed briefly above, the methods described herein can be used to bind a substrate of textured protein or to bind together two or more substrates of textured protein. With reference to FIG. 2, a schematic illustration of binding together multiple substrates 210, 220, 230 is shown. Each substrate 210, 220, 230 may be separately inoculated with mycelium-producing fungi, after which mycelium growth is carried out to bind each substrate individually. As shown in FIG. 2, the substrates 210, 220, 230 can then be layered, after which further inoculant is added to the composite structure 240 and further mycelium growth is carried out. This second round of mycelium growth leads to a matrix forming around all of the substrates 210, 220, 230 such that they are bound together into composite structure 240. While FIG. 2 shows a substrate layering configuration, the substrates can also be placed in any type of touching arrangement.

While FIG. 2 shows three substrates 210, 220, 230 in the form of sheets that are then bound together in sandwich-type configuration, any number of substrates can be bound together using this method, and the substrates being bound together can have any shape and size. In one alternate example, the substrates are in the form of crumbles and are bound together into agglomerates. Furthermore, the substrates bound together in a composite can have a relatively uniform size and/or shape, or the composite can include substrates each having a different size and/or shape.

FIG. 2 shows bringing together three substrate and inoculating the stack to bind together all three substrates at the same time. In an alternative to the embodiment shown in FIG. 2, the substrates 210 and 220 are stacked together, inoculated and bound together by mycelium growth between substrates 210 and 220 to form composite stack 210/220. Subsequently, substrate 230 can be stacked on top of the composite stack 210/220, followed by inoculating the substrates and growing mycelium so that composite stack 210/220 is bound together with substrate 230. This method can be considered a method by which the composite is formed via a series of inoculating and growing steps, one for each substrate added to the previous composite stack.

The method illustrated in FIG. 2 allows for a high degree of variety in preparing the bound composite material. For example, each substrate used in the stack can have a different composition. In one embodiment, substrates 210 and 230 can be substrate of textured vegetable protein, while substrate 220 is a substrate of fungal biomass, such that when the three substrates are bound together, they form a sandwich-type configuration with potentially different flavors, nutrition contents, colors/pigmentation, ingredients (fats, oils, etc.) and/or textures. Each substrate can also be prepared separately from others, such as where some substrates undergoing one or more of processing steps 115, 135, 145 and other substrates either undergo none of processing steps 115, 135, 145 or different version of processing steps 115, 135, 145. Ultimately, a non-homogenous combination of substrates can be created, wherein the non-homogenous combination has a more complex macro texture.

FIG. 2 also clearly illustrates how larger food products can be produced from smaller substrate units. Using the binding technology described herein, these larger composite products have stability and provide food products that may be more suited for mimicking meat or seafood products based on their similarity in size to, e.g., a filet of meat or fish.

Once composite materials are formed, such as via the method illustrated in FIG. 2 and described above, further processing can be carried out to achieve still further complex textures not previously achievable. For example, a crumble product can be created by binding together small substrates using the methods described herein, followed by grounding, crumbling or pulling apart the larger composite product to form crumbles or shreds.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:

1. A method of forming a bound textured substrate comprising:
    inoculating a textured substrate with at least one mycelium-producing fungi, wherein the textured substrate comprises a fungal biomass substrate or a processed fungal fermented composition; and
    growing the mycelium-forming fungi to form a matrix of mycelium inside, outside, or inside and outside of the textured substrate.

2. The method of claim 1, wherein the at least one mycelium-producing fungi comprises a fungus selected from the *Rhizopus* genus or the *Aspergillus* genus.

3. The method of claim 1, wherein growing the mycelium-forming fungi to form a matrix of mycelium comprises a two-stage fermentation process, the first stage comprising a liquid state fermentation process and the second stage comprising a solid state fermentation process.

4. The method of claim 3, wherein the liquid state fermentation process, the solid state fermentation process or both are carried out in an oxygen-enriched environment.

5. The method of claim 1, wherein prior to growing the mycelium-forming fungi to form a matrix of mycelium, the method further comprises:
    compacting, aerating or compacting and aerating the textured substrate.

6. The method of claim 1, wherein prior to, during, or prior to and during growth of the mycelium-forming fungi to form a matrix of mycelium, the method further comprises:
    adding any combination of fat, oil, and carbohydrates to the textured substrate in such a way that the fat, oil and carbohydrates or any combination thereof serve as a feedstock for the mycelium-forming fungi to grow and bind the textured substrate.

7. The method of claim 1, wherein prior to, during, or prior to and during growth of the mycelium-forming fungi to form a matrix of mycelium, the method further comprises:
    adding any combination of color and flavoring to the textured substrate in such a way that the color and flavoring or any combination thereof is taken up by the fungi and becomes a part of the mycelium during growth.

8. The method of claim 1, wherein prior to growing the mycelium-forming fungi to form a matrix of mycelium, the method further comprises:
    sterilizing the textured substrate.

9. The method of claim 1, wherein during growing the mycelium-forming fungi to form a matrix of mycelium, the method further comprises:
    compacting, aerating, or compacting and aerating some or all of the textured, some or all of the grown mycelium, or both.

10. The method of claim 1, wherein after growing the mycelium-forming fungi to form a matrix of mycelium, the method further comprises:
    compacting some or all of the textured substrate, some or all of the grown mycelium or both.

11. The method of claim 1, wherein the textured substrate is a first textured substrate and the method further comprises:
    providing a second textured substrate;
    wherein growing the mycelium-forming fungi to form a matrix of mycelium comprises growing the mycelium-forming fungi inside, outside, or both inside and outside of the first and second textured substrates to bind the first substrate and second substrate together.

12. A bound textured protein substrate comprising:
    at least one textured substrate, wherein the textured substrate comprises a fungal biomass substrate or a processed fungal fermented composition; and
    a matrix of fungal mycelium grown inside, outside, or both inside and outside of the textured substrate.

13. The bound textured protein substrate of claim 12, wherein the fungal mycelium comprises a fungus selected from the *Rhizopus* genus or the *Aspergillus* genus.

14. The bound textured protein substrate of claim 12, wherein the bound textured protein substrate is compacted.

15. The bound textured protein substrate of claim 12, wherein the bound textured protein substrate comprises two or more textured protein substrates and the matrix of fungal mycelium is grown inside, outside, or inside and outside the two or more textured protein substrates to bind together the two or more textured protein substrates.

16. The bound textured protein substrate of claim 15, wherein the two or more textured protein substrate are in the form of layers, and the layers are bound together in a sandwich configuration.

17. The bound textured protein substrate of claim 15, wherein different material is used for at least two of the two or more textured protein substrates.

\* \* \* \* \*